United States Patent
Yoshida et al.

(10) Patent No.: US 7,145,320 B2
(45) Date of Patent: Dec. 5, 2006

(54) PARTICLE COUNTING METHOD AND PARTICLE COUNTER (75) Inventors: Takehito Yoshida, Kawasaki (JP);
Nobuyasu Suzuki, Kawasaki (JP);
Toshiharu Makino, Kawasaki (JP);
Yuka Yamada, Kawasaki (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 370 days.

(21) Appl. No.: 10/762,308

(22) Filed: Jan. 23, 2004

(65) Prior Publication Data

US 2004/0151672 A1 Aug. 5, 2004

Related U.S. Application Data (62) Division of application No. 10/200,499, filed on Jul. 23, 2002, now abandoned.

(30) Foreign Application Priority Data

Jul. 23, 2001 (JP) ............................ P2001-221008
Dec. 28, 2001 (JP) ............................ P2001-400001

(51) Int. Cl.
*G01N 27/00* (2006.01)
*G01N 27/62* (2006.01)
(52) U.S. Cl. ...................... 324/71.4; 324/464; 324/457
(58) Field of Classification Search ................ 324/464, 324/458, 71.3–71.4
See application file for complete search history.

(56) References Cited

U.S. PATENT DOCUMENTS

| | | | |
|---|---|---|---|
| 3,526,828 A * | 9/1970 | Whitby ........................ 324/464 |
| 3,827,217 A * | 8/1974 | Volsy .............................. 96/51 |
| 3,953,792 A | 4/1976 | Fletcher et al. |
| 4,928,065 A * | 5/1990 | Lane et al. .................. 204/549 |
| 5,150,036 A * | 9/1992 | Pourprix ..................... 324/71.4 |
| 6,040,574 A * | 3/2000 | Jayne et al. ................. 250/288 |
| 6,175,227 B1 * | 1/2001 | Graham et al. ............. 324/71.4 |
| 6,281,972 B1 * | 8/2001 | Ebara et al. ................. 356/336 |

FOREIGN PATENT DOCUMENTS

| | | |
|---|---|---|
| JP | 62-043540 | 2/1987 |
| JP | 07-198556 | 8/1995 |
| JP | 2000-077026 | 3/2000 |

OTHER PUBLICATIONS

"Particle Size Measuring Technology" Society of Powder Technology, Daily Industry Newspaper Co., Ltd., (1994), pp. 145-148, (Ryushi-kei Keisoku Gijutsu, Edited by Funtai Kougaku Kai).

* cited by examiner

*Primary Examiner*—Anjan Deb
(74) *Attorney, Agent, or Firm*—Browdy and Neimark, PLLC (57) ABSTRACT

A particle counter counts particles in aerosol having a particle size of from 2 nm to 50 nm in an operating pressure range from an atmospheric pressure through a reduced pressure to a low vacuum and calculate a particle size distribution. The particle counter charges particles in the aerosol and applies an electrostatic field thereto, and mixes the aerosol with a non-charged sheath gas flow shaped like a laminar flow whereby the respective particles separate into traces depending on their particle size where they can be counted. Further, by using an electron multiplier for exciting cluster ions to detect the charged particles and operating it as a high-pass filter, even if the number density of the particles is small, it is possible to effectively count the particles.

2 Claims, 7 Drawing Sheets

PARTICLE COUNTING METHOD AND PARTICLE COUNTER

RELATED APPLICATIONS

This is a division of parent application Ser. No. 10/200,499, filed Jul. 23, 2002 now abandoned.

BACKGROUND OF THE INVENTION

1. Field of the Invention

The present invention relates to measuring and evaluating the particle size distribution of particles in aerosol and, in particular, can quickly and easily measure and evaluate particles having a particle size not more than 100 nm and thus is suitable for in-situ measuring particles in a reduced pressure vapor phase process apparatus and a clean room used for manufacturing a semiconductor integrated device and a liquid crystal display device and contributes to the improvement of the manufacturing yield of these devices.

2. Description of the Related Art

Figure 1:
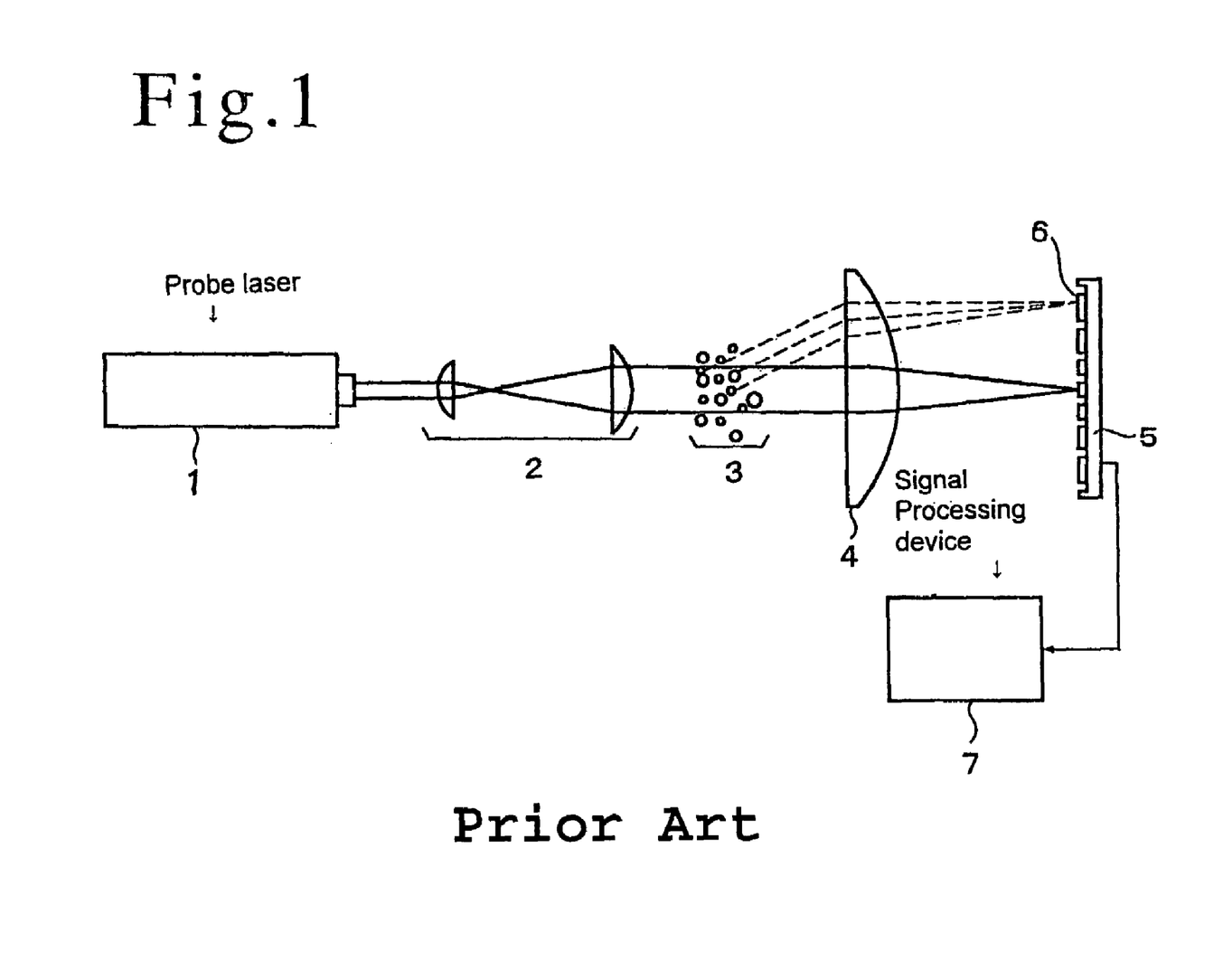
FIG. 1 is a block diagram to show the configuration of a particle counter in the related art.

As an example in the related art, a particle size measuring unit using a laser scattering method, which is a mainstream at present. This is a method of measuring the particle sizes of particles in aerosol and utilizes the phenomenon that when laser light is applied to the aerosol, the spatial intensity distribution of diffracted light of the laser is varied by the distribution of particle size. The constitution and operation to be described below with reference to FIG. 1 are now widely used in the industry concerned, and is disclosed in a literature, for example, "Particle Size Measuring Technology" compiled by Society of Powder Technology, Japan, published by Daily Industry Newspaper Co. Ltd., (1994), Item 145 to Item 148.

A helium-neon (He—Ne) or semiconductor probe laser 1 having an output power of several mW is used as a light source. Its luminous flux is expanded into a parallel luminous flux having a diameter of several mm by a beam expander 2 and is applied to a group of particles 3 in aerosol introduced into a measuring section. In this beam expander 2 is built a spatial filter so as to produce irradiating luminous flux having high parallelism. The laser light scattered by the group of particles in the aerosol is refracted by a receiving lens 4 and is entered into a detector 6 on a focal plane 5. A fθ lens is used as the light receiving lens 4 and the laser luminous flux scattered is collected on the same circumference on the focal plane for each scattering angle. The detector 6 is constituted by semiconductor photoelectric devices arranged on concentric circles the center of which is on the surface of the focal plane to which front scattering (non-scattering) light of the laser luminous flux is applied. This constitution makes it possible to measure the dependence of intensity of the laser light scattered by the particles in the aerosol on the scattering angles. Here, by utilizing that the dependence of intensity of the scattered laser light on the scattering angles depends on the particle distribution of the group of particles, the particle distribution of the group of particles is calculated by a signal processing device 7.

However, since a visible laser is used as the probe light in the related art, a minimum measurable particle size is about 100 nm. This is because if particles to be measured become smaller in size with respect to a probe light wavelength, in particular, smaller than one tenth of the wavelength, they produce Rayleigh scattering in which the dependence of scattering phenomenon on the particle size is hard to observe and thus the particle size distribution can not be calculated by a scattered light intensity distribution. The use of the fourth harmonic of a Nd:YAG laser can produce ultraviolet coherent light (wavelength: 266 nm) by a comparatively small sized apparatus but, even by this light, a minimum measurable particle size is about 40 nm. In order to produce the ultraviolet light having a smaller wavelength, an excimer laser needs to be used, which in turn increases the size of a light source unit and further limits the use of a transmission type lens in an optical system. To realize the ultraviolet light having a smaller wavelength, it is thought to use ultraviolet light having a wavelength of 126 nm, produced by an $Ar_2$ excimer laser, but even if this ultraviolet coherent light is used, a minimum measurable particle size is about 20 nm. On the other hand, a practical design rule in the semiconductor integrated circuit manufacturing technology is 130 nm at present and will be 70 nm in the year of 2008. Further, generally, it is said that a particle size needs to be controlled within a range of one fifth to the design rule. Therefore, it is impossible to control the particles in the semiconductor integrated circuit manufacturing system to keep and improve a manufacturing yield by using the Rayleigh scattering method described above.

SUMMARY OF THE INVENTION

One aspect of a particle counting method in accordance with the present invention is to provide means that charges particles existing in aerosol and then applies an electrostatic field to the aerosol without using light scattering for measurement to thereby get the respective particles into traces depending on their particle sizes and then counts the particles having specific traces.

Further, the method has means that uses an electron multiplier for exciting cluster ions to detect the charged particles and further performs a high-pass filtering, that is, counts particles having particle sizes larger than a specific particle size.

In addition, the method has means that measures the number density of particles having particle sizes larger than a specific particle size on the basis of three or more specific particle sizes by the use of a high-pass filtering operation to thereby predict a particle size distribution in a range covering all particle sizes.

These means can constitute a particle counter capable of quickly and easily measuring and evaluating the particles having particle sizes, in particular, not larger than 50 nm to obtain the particle size distribution of particles in a process aerosol in a reduced pressure vapor phase apparatus.

Further, the particle counting method in accordance with the present invention has means that charges particles existing in the aerosol and then mixes the aerosol with a non-charged sheath gas flow shaped like a laminar flow, applies an electrostatic field to the particles without using light scattering for measurement to thereby get the respective particles into traces depending on their particle sizes, and counts the number of particles having specific traces. Here, without using a bomb gas as a non-charged sheath gas, the atmosphere in a clean zone in which a process apparatus to be measured is disposed is taken in and effectively utilized.

Still further, the method has means that modulates an electrostatic field intensity applied to a classifying tube at a low frequency and amplifies the electric signal of detecting the charged particles tuned to the low frequency in a narrow band in the detection of the charged particles.

In addition, the method has means that applies voltage to a conductive plate, which is disposed after the taken in aerosol is subjected to a charging process and can apply voltage to the flow of aerosol, to electrostatically attract and remove ions floating in the aerosol to thereby improve the accuracy of detecting the charged particles.

These means can constitute a particle counter capable of quickly and easily measuring and evaluating the particles having particle sizes, in particular, not larger than 50 nm to obtain the particle size distribution of particles in a process aerosol in a reduced pressure vapor phase apparatus.

Then, another aspect of the present invention is to provide a particle counting method including the steps of taking in as aerosol a process gas in a process apparatus for conducting a physical or chemical reaction in a reduced vapor phase including a vacuum, and charging particles existing in the aerosol; then applying an electrostatic field to the particles to get the respective particles into traces depending on their particle sizes. By measuring the number of particles having specific traces, it is possible to calculate the particle size distribution of the particles floating in the process device described above.

Further, the present invention is characterized in that an electron amplifier tube for exciting cluster ions is used for detecting the charged particles. This makes it possible to effectively measure particles even if the number density of particles in the sampling aerosol is small.

Still further, the present invention is characterized in that the particles existing in the aerosol are charged and that an electrostatic field is then applied to the charged particles to get the respective particles into traces depending on their particle sizes and that the number of particles having particle sizes larger than a specific particle size is calculated, that is, a high-pass filtering is performed. This can achieve a more effective measurement even if the number density of particles in the sampling aerosol is small.

Still further, the present invention is characterized in that the number density of particles having particle sizes larger than a specific particle size on the basis of three or more specific particle sizes by the use of a high-pass filtering operation. This makes it possible to exert a function of predicting a particle size distribution in a range covering all particle sizes.

In addition, the present invention is characterized in that it includes the steps of: taking in as aerosol a process gas in a process apparatus for conducting a physical or chemical reaction in a vapor phase; charging particles existing in the aerosol; then mixing the aerosol with a non-charged sheath gas flow shaped like a laminar flow and applying an electrostatic field to the particles existing in the aerosol to thereby get the respective particles into traces depending on their particle sizes; and detecting particles having specific traces and measuring the number of particles. This makes it possible to calculate the particle size distribution of the particles floating in the process apparatus.

Here, the present invention is characterized in that atmosphere in a clean zone, in which the process apparatus to be measured is disposed, is taken in as a non-charged sheath gas to reduce a bomb gas accompanying the present apparatus. This makes it possible to simplify the constitution of the preset apparatus.

Further, the present invention is characterized in that, in the detection of the charged particles, an electrostatic field intensity applied to a classifying tube is modulated at a low frequency and the electric signal of detecting the charged particles tuned to the low frequency is amplified in a narrow band. This makes it possible to effectively measure the particle size even if the concentration of particles is low.

Still further, the present invention is characterized in that after taken-in aerosol is charged, a conductive plate capable of applying voltage to the flow of the aerosol is disposed and that voltage is applied to the conductive plate to thereby electrostatically attract and remove floating ions included in the aerosol. This makes it possible to improve the accuracy of detecting the charged particles existing in the aerosol described above.

In addition, the present invention is characterized in that the particles in the aerosol is charged and that the electrostatic field is then applied to the particles to get the particles into traces depending on their particle sizes and that the number of particles having particle sizes close to a specific particle size is calculated. That is, this makes it possible to perform a function of high-pass filtering.

As described above, according to the present invention, there is provided means that charges particles existing in the aerosol and then applies an electrostatic field to the particles to get the respective particles into traces depending on their particle sizes without using light scattering for measurement in a particle counter, to thereby measure the number of particles having specific traces.

Further, there is provided means that uses an electron amplifier tube for exciting cluster ions to detect the charged particles and operates as a high-pass filter to thereby effectively count particles even if the number density of particles is small.

In addition, there is provided means that measures the number density of particles having particle sizes not smaller than a specific particle size by the use of a high-pass filtering operation on the basis of three or more specific particle sizes to predict a particle size distribution in a range covering all particle sizes.

These means can constitute a particle counter capable of quickly and easily in-situ measuring the particles having particle sizes, in particular, not larger than 50 nm to obtain the particle size distribution of particles in a process aerosol in a reduced pressure vapor phase apparatus.

According to the present invention, there is provided means that charges particles existing in the aerosol are charged and then mixes the aerosol with a non-charged sheath gas flow shaped like a laminar flow and applies an electrostatic field to the particles existing in the aerosol without using light scattering for the particle counter to thereby get the respective particles into traces depending on their particle sizes, and counts the number of particles getting the specific traces. Further, there is provided means that modulates an electrostatic field intensity applied to a classifying tube at a low frequency and amplifies the electric signal of detecting the charged particles tuned to the low frequency in a narrow band in the detection of the charged particles, to thereby effectively measure the particles even if the concentration of particles is small. In addition, there is provided means that charges voltage to a conductive plate, which is disposed after taken-in aerosol is subjected to a charging process and can apply voltage to the flow of aerosol, to electrostatically attract and remove floating ions included in the aerosol to thereby improve the accuracy of detecting the charged particles existing in the aerosol described above.

These means can constitute a particle counter that can quickly and easily in-situ measure the particles having particle sizes, in particular, not larger than 50 nm and calculate the particle size distribution.

Therefore, it is the object of the present invention to provide a particle counter capable of counting particles having a particle size ranging from 2 nm to 50 nm in the aerosol in an operating pressure range from the atmospheric pressure through the reduced pressure atmosphere to a low vacuum and calculating a particle size distribution.

The object and advantages of the present invention will be made clearer by the preferred embodiments to be described below with reference to accompanying drawings.

BRIEF DESCRIPTION OF THE DRAWINGS

FIG. 3 is a characteristic curve of the result of measurement and evaluation using a particle counter in accordance with one embodiment of the present invention:

(a) characteristic curve of anode current-electric potential of electric potential applying plate of inner shell cylinder;

(b) characteristic curve of particle number density distribution-electric potential of electric potential applying plate of inner shell cylinder; and (c) a characteristic curve of particle number density distribution-particle size.

DESCRIPTION OF THE PREFERRED EMBODIMENTS

First Embodiment

Figure 2:
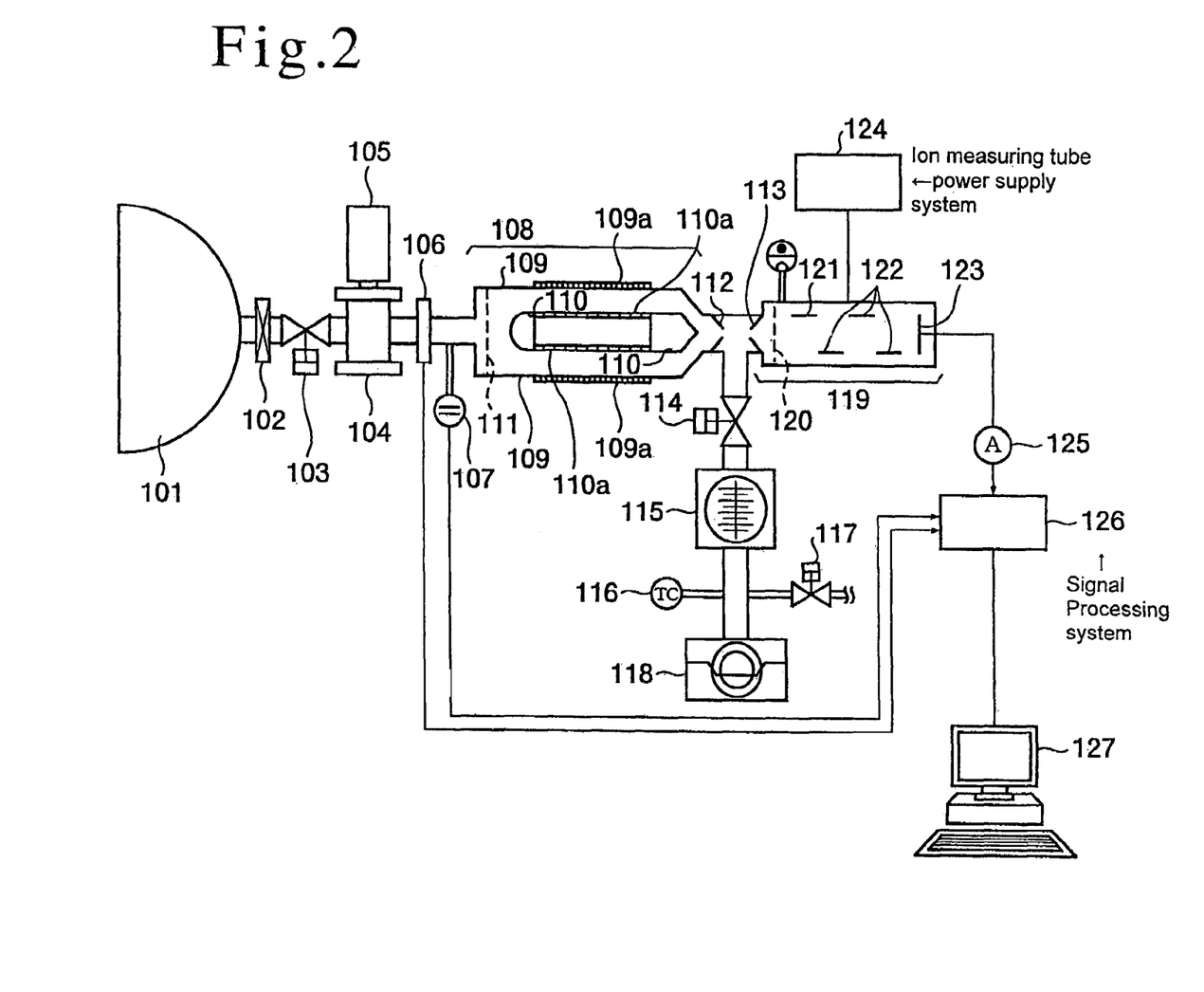
FIG. 2 is a block diagram to show the configuration in accordance with the first embodiment of the present invention.

Next, the preferred embodiment in accordance with the present invention will be described in detail. FIG. 2 is a block diagram to schematically show the general configuration of a particle counter in accordance with the present embodiment. In FIG. 2, a reference numeral 101 denotes a reduced pressure process apparatus process chamber; a reference numeral 102 denotes an aerosol intake valve that is connected to the reduced pressure process apparatus process chamber 101 and takes in aerosol from the reduced pressure apparatus process chamber 101; a reference numeral 103 denotes a intake conductance adjusting valve that adjusts the intake of the aerosol in the aerosol intake valve 102; a reference numeral 104 denotes a charging device that charges the aerosol introduced and a group of particles existing therein; a reference numeral 105 denotes an $Ar_2$ excimer light source that conducts vacuum ultraviolet ray irradiation in a charging process by the charging device 104 described above; a reference numeral 106 denotes a mass flow meter that measures the mass flow of the aerosol; a reference numeral 107 denotes a capacitance manometer that measures an operating pressure in a particle classifying tube (to be described later); a reference numeral 108 denotes the particle classifying tube into which the aerosol whose mass flow is measured by the mass flow meter 106 is introduced and which classifies particles in the aerosol.

The particle classifying tube 108 usually has a cylindrical structure, that is, a double cylindrical structure including an outer shell cylinder 109 constituting its outer shape and an inner shell cylinder 110 forming the inside of the outer shell cylinder 109 in a nearly annular shape. The outer shell cylinder 109 is electrically insulated from the inner shell cylinder 110. Near the inlet or the uppermost stream portion of the particle classifying tube 108 is provided a sheet mesh 111. Near the outlet of the particle classifying tube 108 is provided an orifice 112. Further, an electric potential applying plate 109a is mounted on the outside wall of the outer shell cylinder 109, whereas an electric potential applying plate 110a is mounted on the outside wall (outside wall on the inner diameter side with respect to the aerosol passage) of the inner shell cylinder 110.

A reference numeral 114 denotes an exhaust system conductance adjusting valve that adjusts the exhaust of the aerosol. A reference numeral 115 denotes a high-pressure-operated helical pump that is the main body of a large-capacity exhaust system. A reference numeral 116 denotes a thermocouple gage. A reference numeral 117 denotes a leak valve that discharges the exhausted aerosol. A reference numeral 118 denotes a scroll pump. The constituent parts of the exhaust system conductance adjusting valve 114, the high-pressure-operated helical pump 115, the thermocouple gage 116, the leak valve 117, and the scroll pump 118 constitute the large-capacity exhaust system that exhausts the aerosol.

Further, a reference numeral 119 denotes a multiplier ion measuring pipe. The multiplier ion measuring pipe 119 has an ion cathode 120 that discharges electrons by the collision impact of a group of particles (that are called also charged cluster ions) jetted out of the orifice 112 and introduced into the multiplier ion measuring pipe 119, an electron producing dynode 121 that is provided next to the ion cathode 120 and produces many electrons by the group of electrons discharged by the impact caused by the cluster ions, an electron multiplying dynode 122 at the last stage, and an anode 123 that is provided next to the electron multiplying dynode 122 and is set at an electric potential higher than the electron multiplying dynode 122. At the inlet of the multiplier ion measuring pipe 119, a skimmer 113 is provided opposite to the downstream side of the orifice 112.

Further, a reference numeral 125 denotes an ammeter that measures the micro current of the anode 123. A reference numeral 126 denotes a signal processing system that collects and processes various kinds of numerical values necessary for classifying and measuring the particles. A reference numeral 127 denotes a personal computer that performs a computation necessary for processing the signal of the signal processing system 126.

The operation of the particle counter having the configuration described above will be described. The particle counter of the present embodiment is connected in a vapor phase to the process chamber 101, in particular, in a chemical vapor deposition (CVD) or a physical vapor deposition (PVD), which is conducted in a reduced pressure gaseous phase, or a dry etching in a semiconductor integrated circuit manufacturing process system in conformity with an ultra-fine design rule (130 nm or less). The particle counter has, as a whole, a function of reducing pressure or exhausting to a vacuum.

The aerosol that is introduced into the particle counter via the aerosol intake valve 102 to constitute a process atmosphere has its mass flow adjusted by the intake conductance 
adjusting valve 103. This is because while the particle classifying tube 108 requires as large an aerosol mass flow as possible, the multiplier ion measuring pipe 119 mounted next to the particle classifying tube 108 needs to be operated under as high a vacuum as possible.

Next, the introduced aerosol and the group of particles existing therein are charged by the charging device 104. While vacuum ultraviolet rays irradiated from the $Ar_2$ excimer laser light source 105 operated under a wide range of aerosol gas pressure is used in this charging process in the present embodiment, it is also recommended that a radioisotope, a direct-current corona discharge, an ion beam, an electron beam be used (in the decreasing order of operating gas pressure), depending on the operating gas pressure. In particular, in a high vacuum of $10^{-3}$ Pa or less, it is effective to use the ion beam or the electron beam that can charge the particles into a single polarity.

The aerosol has its mass flow measured by the mass flow meter 106 and then is introduced into the particle classifying tube 108. Here, since the capacitance manometer 107 is provided just before the particle classifying tube 108 and thus a pressure drop between them is extremely small, the operating gas pressure in the particle classifying tube 108 can be measured.

Although the particle classifying tube 108 is shown as a cross-sectional schematic view in FIG. 2, it has the double-cylindrical structure that is basically constituted by the outer shell cylinder 109 and the inner shell cylinder 110. The introduced aerosol goes to the downstream side, in a laminar state, in the gap between the outer shell cylinder 109 and the inner shell cylinder 110, which are electrically insulated from each other. The sheet mesh 111 is provided at the uppermost stream side to help the flow of the aerosol in the particle classifying tube 108 to become a laminar flow.

The aerosol becomes a laminar flow in the particle classifying tube 108 and flows in the gap between the outer shell cylinder 109 and the inner shell cylinder 110 from the upstream side to the downstream side (in FIG. 2, from the left side to the right side in the horizontal direction) at a constant speed. Here, since the mass flow of the aerosol is monitored by the mass flow meter 106 and the cross-sectional area of the flow passage is already known, the average speed in the horizontal direction of the aerosol and the particles therein can be easily obtained. On the other hand, the outer shell cylinder 109 and the inner shell cylinder 110 are independent of (electrically insulated from) each other and further are provided with the electric potential applying plates 109a, 110a (portions longitudinally hatched in FIG. 2), respectively.

If the electric potential applying plate 109a of the outer shell cylinder 109 is made a ground potential and the electric potential applying plate 110a of the inner shell cylinder 110 is fixed at a negative electrostatic potential, an electrostatic field is generated concentrically from the outer side to the inner side (in the vertical direction in FIG. 2) in the double-cylindrical cross section. If the aerosol is in a viscous fluid range, the particles existing in the aerosol is drifted in the direction of the concentric center at a speed corresponding to the product of a mobility Z and an electric field intensity E. Thus, the group of particles move at the resultant speed of the speed in the same horizontal direction, caused by the flow of the aerosol, and the speed in the direction of the concentric center, caused by the electric field drift vertical to the flow of the aerosol. Since the mobility Z of the particle in the viscous fluid is approximately determined by the cross-sectional area of the particle, the group of particles moves in different traces in accordance with the respective particle sizes. Naturally, as the particle is smaller in size, it tends to be polarized from the horizontal direction speed, and as the particle becomes larger in size, it tends to keep the original horizontal direction speed.

As a result, the particles larger than a certain particle size pass through the particle classifying tube 108, the orifice 112, and the skimmer 113 and reach the multiplier ion measuring tube 119, whereas the particles smaller than the certain particle size are attached to the electric potential applying plate 110*a* of the inner shell cylinder 110 side, if the particles are charged positively, or the electric potential applying plate 109*a* of the outer shell cylinder 109 side, if the particles are charged negatively. In general, once the particles in the range of nanometer are collided with the wall of the device, they remain being attracted at the portions. The certain particle size described above means the boundary size of a particle that passes through or is attracted by the particle classifying tube 108 and is determined by the geometrical shape of the particle classifying tube 108, the flow rate of the aerosol, and the electrostatic field intensity. In practice, the boundary size of a particle passing or being attracted is adjusted by varying the electrostatic field intensity having the largest range of variability. It is said that the particle classifying tube 108 shows an operation as a high pass filter because it can measure the particles while shutting off all the particles smaller than the set particle size.

The downstream side of the orifice 112 is set at a pressure of the order of $10^{-4}$ Torr, or a range of molecule rays by a pressure loss caused by the orifice 112 of low conductance and the large-capacity exhaust system having the high-pressure-operated helical pump 115 as a main body. The group of particles jetted out of the orifice 112 (that can be called also charged cluster ions) pass through the skimmer 113 and collide with the ion cathode 120 that is the first stage of the multiplier ion measuring tube 119. In the ion cathode 120, electrons are discharged by the collision impact of the cluster ions. Since the ion cathode 120 is fixed at a negative electric potential of several V to several tens V, the cluster ions charged positively are accelerated by the electrostatic field even after they pass through the skimmer 113, thereby being supplied with collision energy large enough to ionize atoms on the surface of the ion cathode 120 and to discharge electrons.

The group of electrons discharged by the collision impact of the cluster ions charged positively fly to and collide with the electron producing dynode 121, which is disposed at the next stage and is fixed at the higher electric potential, to produce many electrons there. Usually, the number of produced electrons is larger than that of collided electrons, that is, a multiplier effect can be realized. This operation is repeated several times (4 times in FIG. 2) between the electron multiplier dynodes in the multiplier ion measuring tube 119, which finally achieves a multiplier factor of about $10^6$. The many groups of multiplied electrons are recovered by the anode 123 fixed at a higher potential than the electron multiplier dynode 122 at the last stage and are measured by the ammeter 125 for measuring the micro current.

In setting the electric potential between the ion cathode 120, the electron producing dynode 121, the electron multiplying dynode 122 and the anode 123 in the multiplier ion measuring tube 199, assuming that the entering cluster ions are positively charged, the ion cathode 120 is set at minus several V to minus several tens V and the anode 123 is set at a high electric potential of plus 1000 V to plus 3000 V, wherein the high electric potential described above are equally distributed among the electron producing dynode 121 and three stages of electron multiplying dynodes 122.

The electric potential in the multiplier ion measuring tube 119 is set by an ion measuring tube power supply system 124. Here, in order to easily discharge electrons, the alloy of alkaline and alkaline-earth metal having a small work function is vapor deposited on the surfaces of the ion cathode 120, the electron producing dynode 121, and the electron multiplying dynode 122.

Figure 3A:
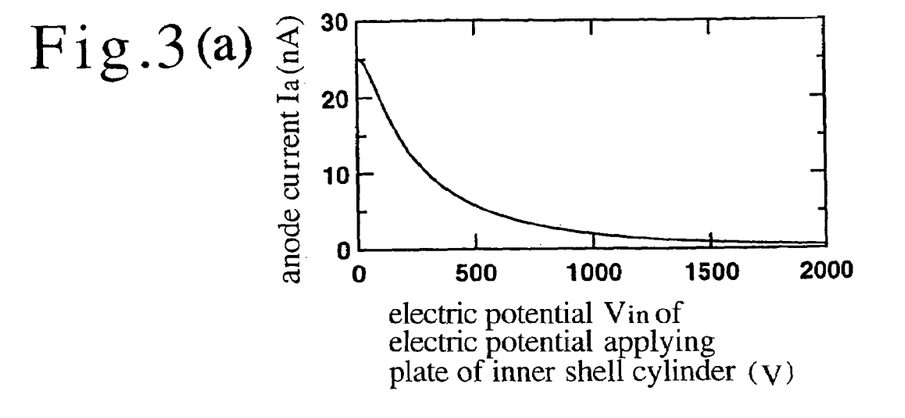

The various kinds of numerical data necessary for classifying and measuring the particles, that is, the mass flow of the aerosol measured by the mass flow meter 106, the pressure of the aerosol measured by the capacitance manometer gage 107, the electric potential of the electric potential applying plate 110a of the inner shell cylinder 110 of the particle classifying tube 108, the micro current measured by the ammeter 125 (anode current) are collected by the signal processing system 126 and are converted into digital signals that can be easily processed by the personal computer 127. In a usual method of displaying data, the electric potential of the electric potential applying plate 110a of the inner shell cylinder is scanned with the mass flow and the pressure of the aerosol kept at fixed vales and the current value of the ammeter 125, which increases or decreases in accordance with the scanning, is displayed. A typical measurement example is shown in FIG. 3(a) where the potential $V_{in}$ of the potential applying plate 110a of the inner shell cylinder is plotted on a horizontal axis in an absolute value and where an anode current $I_a$ is plotted on a vertical axis. The particle classifying tube 108 acts as a high pass filter as a whole. As the absolute value $V_{in}$ increases, the maximum particle size of all the particles which can not pass (are shut off by) the particle classifying tube 108 increases and thus the characteristic curve in FIG. (a) monotonously decreases.

Figure 3B:
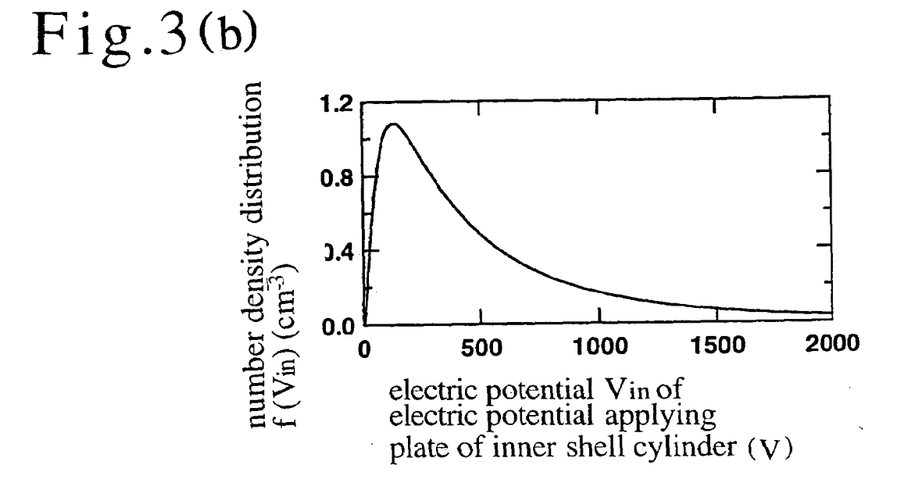
Figure 3C:
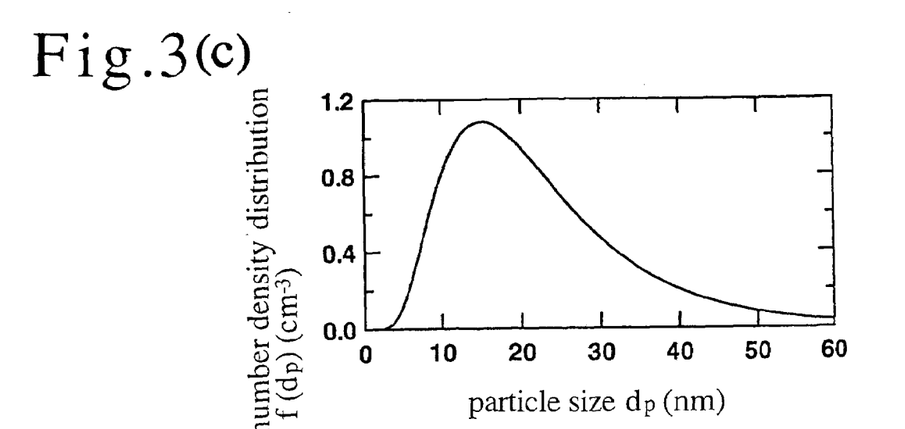

Next, assume that when the voltage $V_{in}$ is applied to the particle classifying tube 108, the maximum particle size of all the particles which are shut off by the particle classifying tube 108 is $d_p$ and its number density distribution is f. Taking into account a function of $V_{in}$ in accordance wit the FIG. 3(a), and $I_a$ and f are combined with each other by the following relationship (Equation 1).

$$\frac{I_a}{Q_c} \propto \int_{V_{in}}^{\infty} f(V_{in}) dV_{in} \qquad \text{(Equation 1)}$$

Where $Q_c$ is the flow rate of a carrier gas. That is, by standardizing and differentiating the characteristic curve (FIG. 3(a)) of $I_a$ measured while sweeping $V_{in}$ by and with respect to the flow rate of carrier gas, the number density distribution f can be obtained as a function of $V_{in}$. This will be shown in FIG. 3(b). Further, the following relationship (equation 2) holds between $V_{in}$ and $d_p$.

$$d_p(V_{in}) = \frac{2\pi e C_c L}{3\pi \mu Q_c \ln(R_2/R_1)} V_{in} \qquad \text{(Equation 2)}$$

Where e is a charge elementary quantity; $C_c$ is Cunningham's correction factor; $\mu$ is the viscosity of the carrier gas; $Q_c$ is the flow rate of the carrier gas; L is the classifying length of the particle classifying tube (length of the electric potential applying plate); $R_1$ is the radius of the inner shell cylinder of the particle classifying tube; and $R_2$ is the radius of the outer shell cylinder of the particle classifying tube. The use of the relationship of the equation 2 makes it possible to convert the number density distribution f into a function of the particle size $d_p$, that is, a particle size distribution function. The result of conversion will be shown in FIG. 3(c). This corresponds to the particle spatial number density of the reduced pressure apparatus process chamber 101 that is the object to be measured. In the present preferred embodiment, the mathematical transformation described above is processed by the computer 127, so that the particle size distribution function $f(d_p)$ of the space to be measured can be calculated from the data of $V_{in}$ and $I_a$ which are directly measured. This measurement and evaluation method fundamentally makes it possible to conduct measurement during the process operation, that is, an in-situ measurement.

Further, in the present preferred embodiment, even when a helium gas is used as the carrier gas, if the pressure of the carrier gas in the particle classifying tube 108 is 5 Torr or more, the particle having a size of 2 nm or more can be sufficiently classified. As the flow rate of the carrier gas, the pressure of the gas to be classified, and the molecular size of the carrier gas become larger, the accuracy of classification tends to be improved.

Still further, if the characteristics of the particle size distribution function $f(d_p)$ (which becomes a logarithmic normal distribution in many cases) for each reduced pressure apparatus process chamber 101 are stored by repeating the continuous sweeping of $V_{in}$ several times, thereafter, it is also possible to more quickly estimate and evaluate the particle size distribution function $f(d_p)$ from about three measurement results of $V_{in}$.

Second Embodiment

Figure 4:
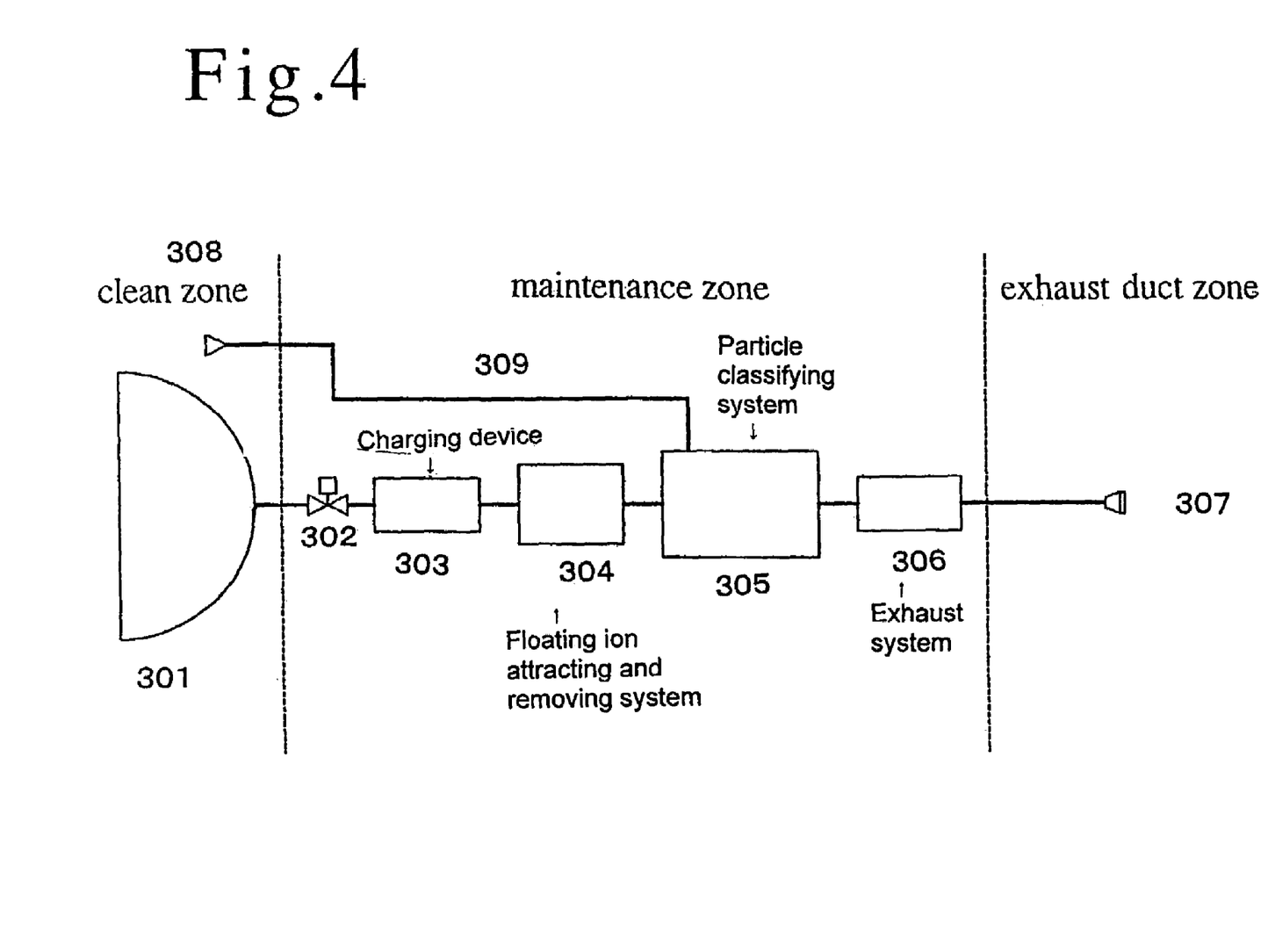
FIG. 4 is a block diagram to show the general configuration of a particle counter in accordance with one embodiment of the present invention.

Next, the second embodiment in accordance with the present invention will be described in detail. FIG. 4 is a block diagram to show the general configuration of a particle counter in accordance with the present embodiment. The particle counter of the present embodiment is connected in a vapor phase to a process chamber 301, in particular, in a chemical vapor deposition (CVD) or a physical vapor deposition (PVD) that is conducted in a reduced pressure vapor phase or a dry etching in a semiconductor integrated circuit manufacturing process system in conformity with an ultra-fine design rule (130 nm or less). In the present embodiment, the process chamber 301 is a process apparatus conducting a physical or chemical reaction in the vapor phase, and has a function as an aerosol supply source.

This particle counter is provided with an aerosol intake valve 302 connected to the process chamber 301, a charging device 303 for charging the aerosol introduced from the aerosol intake valve 302 and a group of particles existing in the aerosol, a floating ion attracting and removing system 304 for attracting and removing floating ions that interfere with the measurement of the charged particles charged by the charging device 303, a particle classifying system 305 for classifying the group of charged particles from which the floating ions are attracted and removed, and an exhaust system 306 that is provided at the last stage of the particle counter and differentially exhausts the whole particle counter.

Further, the particle counter has a sheath gas carrying line 309 in parallel to the configuration connected in the vapor phase to the process chamber 301, as described above. The sheath gas carrying line 309 is connected to a sheath gas intake port 308 made separately from the process chamber 301 and cleans air is introduced as a sheath gas from the sheath gas intake port 308. The sheath gas is introduced into the sheath gas carrying line 309 into the particle classifying system 305.

This configuration provides the particle counter as a whole with a function of reducing pressure thereof or exhausting itself to a vacuum. That is, during the operation of the particle counter, exhausting the particle counter differentially by the exhaust system 306 provided at the last stage forms the forward flow of the aerosol to be measured from the process chamber 301 at the first stage to the exhaust system at the last stage.

The process atmosphere aerosol introduced into the particle counter via the aerosol intake valve 302, firstly, has its mass flow adjusted by the flow-rate adjusting function of the aerosol intake valve 302. This is because in the particle classifying system 305, a large mass flow is required to improve a particle classifying ability but too big mass flow increases the electrostatic field intensity necessary for classification to a value exceeding a practical range.

Next, the aerosol introduced and the group of particles existing in the aerosol are charged by a charging device 303. In the present embodiment, an $Ar_2$ excimer light source to be operated during the charging process under a wide range of the aerosol gas pressure is provided in the charging device 303 and vacuum ultraviolet rays irradiated from the $Ar_2$ excimer laser light source is used. It is also recommended that, depending on the operating gas pressure, an radioisotope, a direct-current corona discharge, an ion beam, or an electron beam be used appropriately (in the decreasing order of the operating gas pressure). In particular, in a high vacuum of $10^{-3}$ Pa or less, it is effective to use the ion beam or the electron beam that can charge particles into a unipolar state.

The aerosol subjected to the charging process is introduced into the floating ion attracting and removing system 304 and the floating ions that interfere with the measurement of the charged particles to be measured are attracted and removed there. Needless to say, the floating ions are extremely smaller than the particles to be measured (particle size range: 2 nm to 50 nm) and thus their electric mobilities in a viscous gas are extremely small. The floating ions are produced by a plasma process in the reduced process apparatus chamber 301 and the charging process in the charging device 303.

Figure 5:
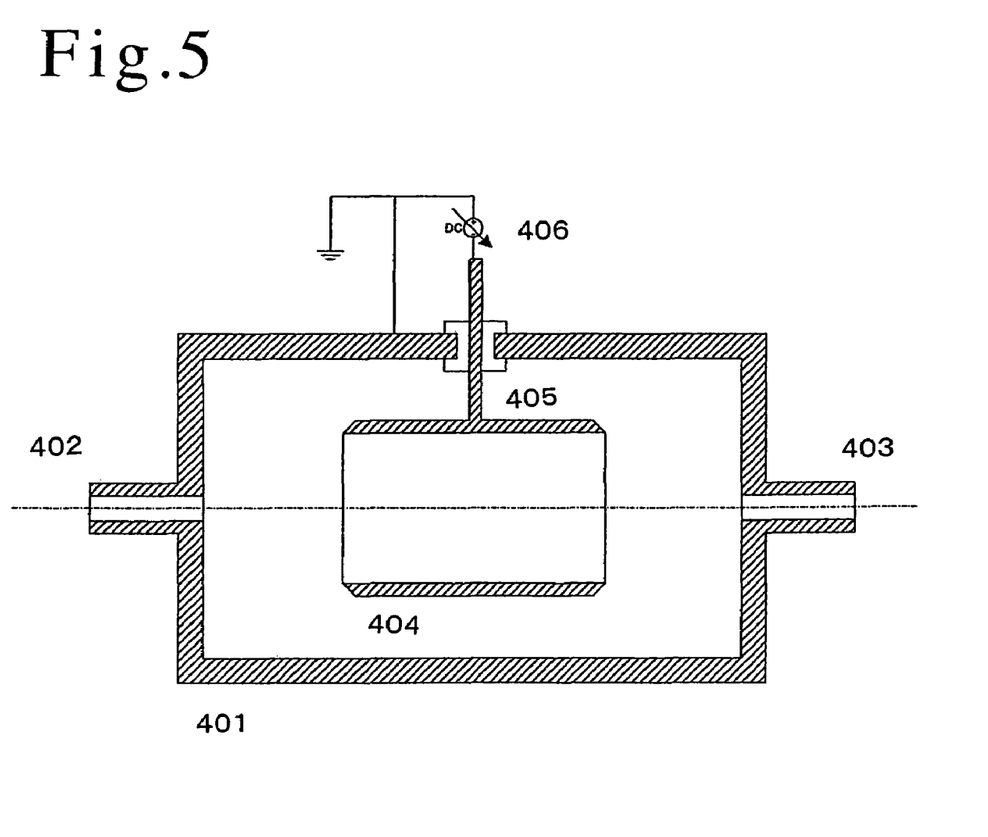
FIG. 5 is a cross-sectional configurational view of a floating ion attracting and removing chamber that is a constituent part of a particle counter in accordance with one embodiment of the present invention.

FIG. 5 is a cross-sectional configurational view of a floating ion attracting and removing chamber constituting the floating ion attracting and removing system 304 of the particle counter in the present embodiment. This floating ion attracting and removing chamber 401 is provided with a chamber body 401a having a hollow cylindrical structure, an aerosol introduction port 402 for introducing the charged particles charged by the charging device 303, an aerosol discharge port 403 for discharging the group of charged particles from which the floating ions are attracted and removed, a floating ion attracting cylinder 404 that is disposed in the hollow space of the chamber body 401a and attracts and removes the floating ions, an attracting cylinder suspending bar 405 for suspending the floating ion attracting cylinder 404 to dispose the floating ion attracting cylinder 404 in the hollow space of the chamber body 401a, and an electric potential applying device 406 that is connected to the attracting cylinder suspending bar 405 and applies an electrostatic potential to the floating ion attracting cylinder 404 via the attracting cylinder suspending bar 405. The chamber body 401a and the floating ion attracting cylinder 404 are coaxially arranged.

The operation of the floating ion attracting and removing chamber 401 having such a constitution will be described. The floating ion attracting and removing chamber 401 has a constitution in which the aerosol flow supplied from the charging device 303 passes through the inside thereof along the rotational central axis. The aerosol flowing into the chamber 401 through the aerosol introduction port 402 passes through the inside of the floating ion attracting cylinder 404 that has a hollow cylindrical shape and has the same rotational central axis as the chamber body 401a and flows out from the aerosol discharge port 403. Here, the floating ion attracting cylinder 404 is made of good conductive metal (oxygen-free copper or SUS304) and is held by an attracting cylinder suspending bar 405 that is insulated from the wall of the chamber body 401 itself. The attracting cylinder suspending bar 405 is made of the same good conductive metal as the floating ion attracting cylinder 404 and is connected to an electric potential applying device 406, whereby a negative electric potential is electrostatically applied to the floating ion attracting cylinder 404. The magnitude of the negative electric potential of the floating ion attracting cylinder 404 is set, in view of the flow rate (residence time in the floating ion attracting and removing chamber 401) of the aerosol and the gas pressure (that determines the electric mobilities of the ions and particles existing in the aerosol), such that the floating ions are electrostatically deflected from the starting direction of velocity of flow and attracted by the ion attracting cylinder 404 and that the charged particles (2 nm to 50 nm) are not attracted by but can pass through the ion attracting cylinder 404.

In the floating ion attracting and removing chamber 401, the aerosol passing the floating ion removing process is introduced into the particle classifying system 305 shown in FIG. 4 where the group of charged particles existing in the aerosol are classified according to the values of electric mobilities depending on the particle sizes. The principle of classification of the charged particles will be described in more detail with reference to FIG. 7.

Figure 6:
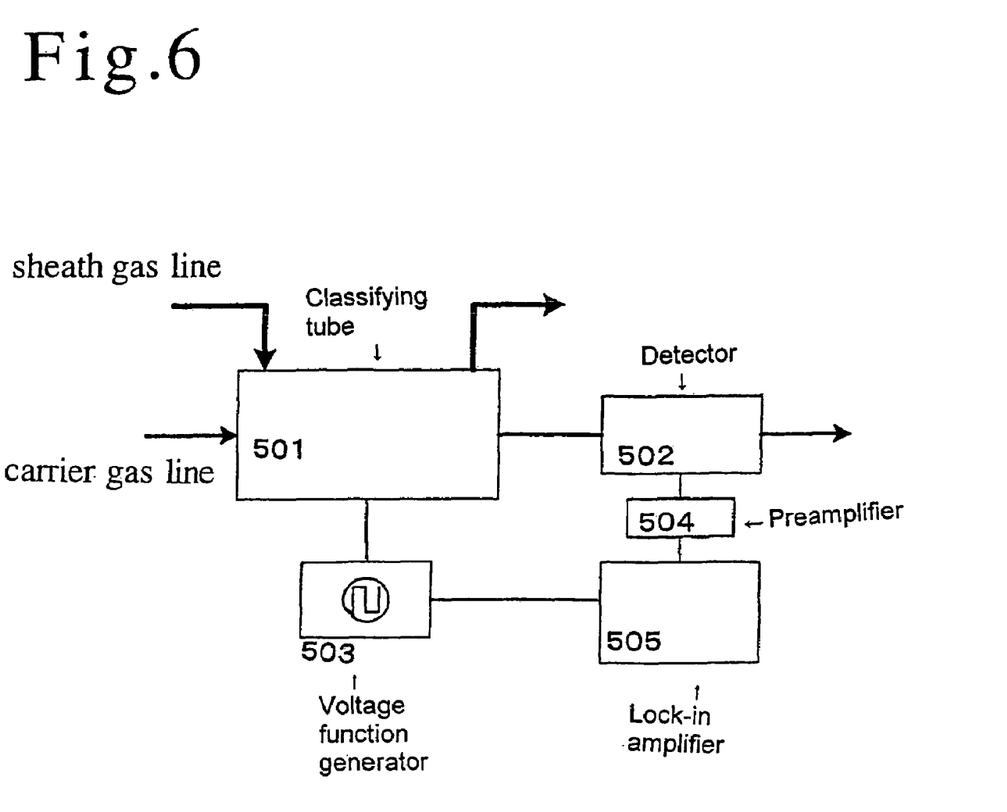
FIG. 6 is a block diagram to show the configuration of a particle classifying system that is a constituent part of a particle counter in accordance with one embodiment of the present invention.
Figure 7:
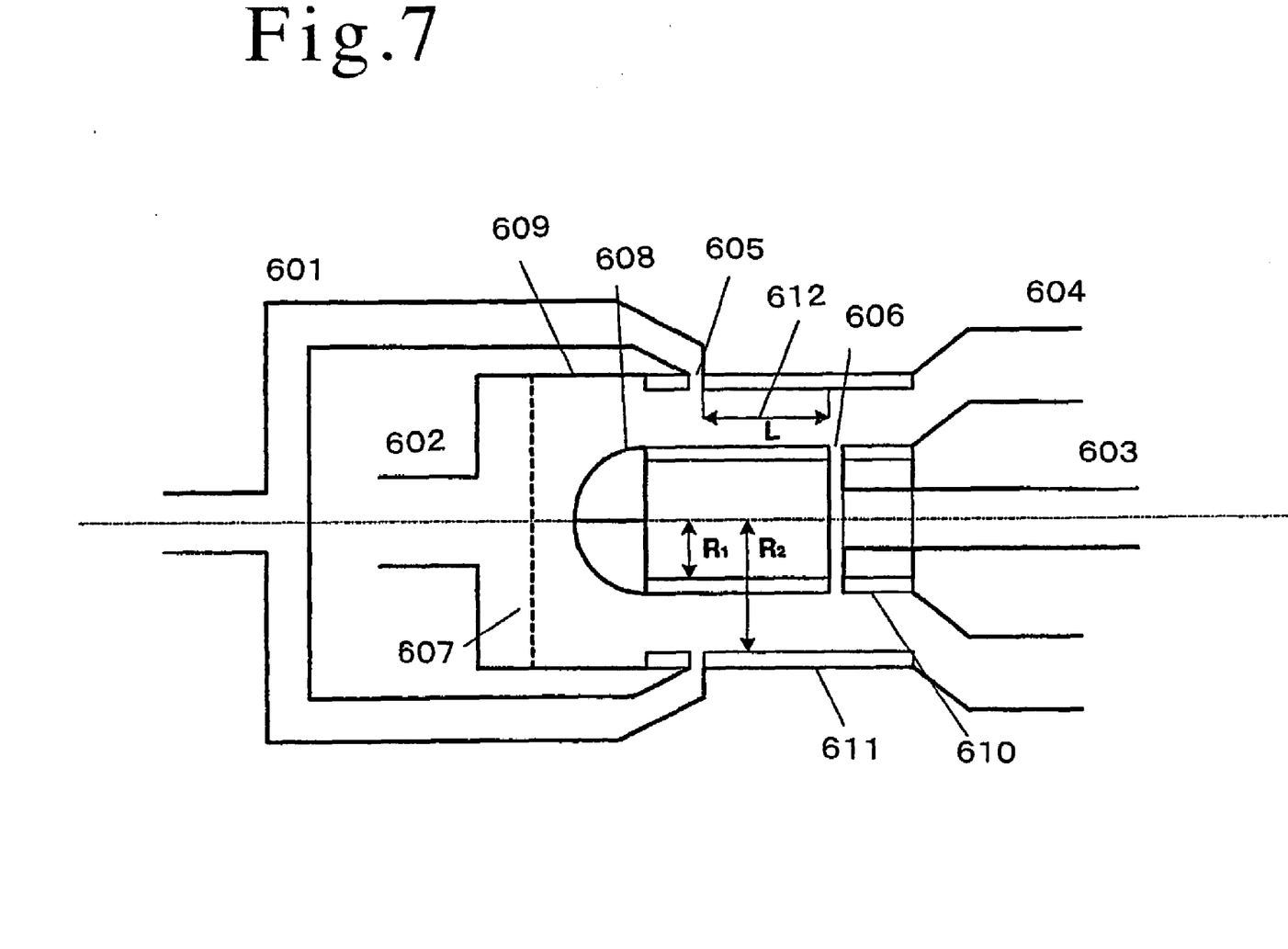
FIG. 7 is a cross-sectional configurational view of a classifying tube of a particle classifying system that is a constituent part of a particle counter in accordance with one embodiment of the present invention.

FIG. 7 is a cross-sectional configurational view of the classifying tube 501 (see FIG. 6) constituting the particle classifying system 305 of the particle counter in the present embodiment. The classifying tube 501 is provided with a carrier gas introducing line 601 for introducing the aerosol from which the floating ions are removed in the floating ion attracting and removing chamber 401, a sheath gas introducing line 602 connected to the sheath gas carrying line 309, a classified aerosol discharge port 603 for discharging the classified aerosol containing the charged particles, and a sheath gas discharge port 604 for discharging the sheath gas introduced from the sheath gas introducing line 602 through the exhaust system 306.

Further, the classifying pipe 501 is provided with an aerosol jetting-out slit 605 for introducing the aerosol to be measured, which is introduced into the carrier gas introducing line 601, into a classifying region (shown by a reference character L in FIG. 7); an aerosol introducing slit 606 for introducing the aerosol classified in the classifying region L from the classifying region L into the classified aerosol discharge port 603; a filter mesh 607 for filtering the sheath gas introduced from the sheath gas introducing line 602 to make the sheath gas into a laminar flow; an inner shell cylinder 608 that becomes an inside shell for forming the classifying region L; and an outer shell cylinder 609 that is arranged so as to cover the outside of the inner shell cylinder 608 and becomes an outside shell for forming the classifying region L along with the inner shell cylinder 608.

Still further, the classifying tube 501 is provided with a positive high-voltage electrode 610 placed on the outside wall of the inner shell cylinder 608 and a ground electrode 611 that is placed on the inside wall of the outer shell cylinder 609 and produces an electrostatic electric field when voltage is applied across itself and the above-mentioned positive high-voltage electrode 610. The inner shell cylinder 608 and the outer shell cylinder 609 are arranged such that they have the same central axis.

The operation of the classifying tube 501 having the configuration like this will be described. In the present embodiment, first, clean air is introduced as a sheath gas at a flow rate of 2.5 l/min through the sheath gas introducing line 602. This clean air is taken from a clean zone (class 1 or less) in which a reduced pressure process apparatus is disposed through the sheath gas taking-in port 308 in the general configurational view of the particle counter shown in FIG. 4 and is introduced through the sheath gas carrying line 309. The sheath gas is introduced into the space formed between the inner shell cylinder 608 and the outer shell cylinder 609 (which becomes the classifying region L in a limited meaning) through the filter mesh 607, thereby being effectively made a laminar flow in the classifying region L. Here, the inner shell cylinder 608 and the outer shell cylinder 609 are arranged such that their rotational central axes are parallel and concentric to the sheath gas flow. The sheath gas having the same flow rate as the introduced sheath gas is discharged from the sheath gas discharge port 604 by the exhaust system 306. The exhaust system 306 is constituted by a dry mechanical pump or a combination of the dry mechanical pump and a high-pressure-operated turbo-molecular pump arranged at its preceding side. On the other hand, the aerosol to be measured is introduced into the classifying region L at a flow rate of 0.5 l/min through the carrier gas introducing line 601 from the aerosol jetting-out slit 605.

In the classifying region L, a radial electrostatic electric field is applied to the common central axis by the positive high-voltage electrode 610 placed on the outside wall of the inner shell cylinder 608 and the ground electrode 611 placed on the inside wall of the outer shell cylinder 609. The particles existing in the aerosol, which are introduced from the aerosol jetting-out slit 605 into the classifying region L and are not charged (charging efficiency of the charging device 303 is smaller than 1), are carried with the sheath gas flow shaped like a laminar flow from the aerosol jetting-out slit 605 to the direction of the sheath gas discharge port 604 (from the left to the right in FIG. 7) and are discharged from the sheath gas discharge port 604. The particles existing in the aerosol, which are charged by the charging device 303, are deflected by the electrostatic field formed in the classifying region L. In particular, the particles negatively charged are attracted to the side of the inner shell cylinder 608 side and part of them can be discharged from the classified aerosol discharge port 603 through the aerosol introducing slit 606.

The trace of the charged particle in the classifying region L, in principle, is determined by the mobility (particle size) of the charged particle in the sheath gas, a lateral carrying speed by the sheath gas, an electrostatic field intensity distribution, a geographical shape (length of the classifying region L, diameter of the inner shell cylinder $R_1$, diameter of the outer shell cylinder $R_2$). By setting these parameters appropriately, particles of a special particle size can be extracted from the classified aerosol discharge port 403, that is, can be classified. Usually, the central value of the particle size after classification is determined by setting the lateral carrying speed and the geographical shape and finally by adjusting the electrostatic field intensity (as a soft parameter), the particle size after classification can be arbitrarily selected. Measuring the number of charged particles after classification (spatial number density) by the use of the ammeter measuring a micro current while scanning the electrostatic field intensity makes it possible to calculate and evaluate the particle size distribution of the particles existing in the aerosol to be measured.

Next, the constitution of a signal detecting section and the operation of detecting a signal in the particle classifying system 305 will be described with reference to FIG. 6. The detection of the signal in the embodiment of the particle counter in accordance with the present invention is based on measuring the number of charged particles existing in the aerosol flow after classification, that is, the spatial number density by the use of the ammeter. Here, it is the case where the number density of the floating ions can not neglected as compared with the number density of charged particles to be measured that presents a problem. As described already also in the present embodiment, the floating ions are removed by the use of the floating ion attracting and removing chamber 401 but can not be sufficiently removed in many cases. In other words, even if the floating ions are removed and classified from the charged particles of specific particle size by the electrostatic attraction or deflection, the effect (flowing into the ammeter) of the floating ions scattered in the whole aerosol flow passage of the particle counter by a vapor phase diffusion phenomenon presents a problem.

In the present embodiment, therefore, by modulating the electrostatic field intensity applied to the classifying operation in the classifying tube 501 at low frequency (several Hz to several tens Hz), the charged particles reaching the ammeter for detection are shut off by the modulation frequency. By amplifying only this modulation frequency component in a narrow band, it is intended to remove the effect of the floating (diffused) ions constantly flowing into the ammeter.

FIG. 6 is a block diagram to show the constitution of the signal detecting section of the particle counter classifying system 305. The signal detecting section is provided with a detector 502 disposed at the downstream of the classified aerosol discharge port 603, a voltage function generator 503 for generating the electrostatic field for the classification operation of the classifying tube 501, a preamplifier 504 for converting a current signal representing the number of charged particles after classification measured by the detector 502 into a voltage signal, and a lock-in amplifier 505 for amplifying the signal converted into the voltage signal by the preamplifier 504 in a narrow band by the modulation frequency described above.

In the signal detecting section having the constitution like this, an electrostatic field of a rectangular waveform is applied to the classifying tube 501 for its classifying operation by the voltage function generator 503. This electrostatic field has a frequency of several Hz, a duty ratio of 1/2, a maximum application voltage by which all particles of the particle size to be measured (50 nm or less) are deflected and attracted to the wall of the inner shell cylinder 608 on the upstream side of the aerosol taking-in slit 606, and a minimum application voltage by which particles of a specific particle size to be measured are made to reach the aerosol jetting-out slit 606. The number of charged particles after classification is measured as a current signal by the detector 502 whose main part is the ammeter disposed on the down stream side of the classified aerosol discharge port 603. This current signal is converted into a voltage signal by the preamplifier 504 and then is amplified in a narrow band by the modulation frequency described above. Here, as a reference frequency signal, the same waveform that generates the electrostatic filed for classifying operation is applied by the voltage function generator 503.

While the present invention has been described based on the preferred embodiments shown in the drawings, it is clear to the person skilled in the art that the present invention can be easily changed or modified and those changes and modifications will be included within the spirit and scope of the present invention.

What is claimed is:

1. A particle counting method, comprising the steps of:
   taking in as aerosol flow a process gas in a process apparatus disposed in a clean zone for conducting a physical or chemical reaction in a vapor phase;
   charging particles existing in the aerosol flow;
   applying voltage to a conductive cylinder disposed in the aerosol flow having been subjected to the charging process to thereby electrostatically attract and remove floating ions included in the aerosol;
   then introducing clean air from the clean zone and generating a non-charged sheath gas flow shaped like a laminar flow in the periphery of the conductive cylinder disposed in the aerosol flow and mixing the sheath gas flow with the aerosol flow, and then applying an electrostatic field to the conductive cylinder to thereby classify the particles existing in the aerosol flow by getting the respective particles into traces deflected depending on their particle sizes; and
   detecting particles having specific traces deflected and measuring the spatial number density of particles to thereby calculate the particle size distribution of the particles floating in the process apparatus.

2. A particle counting method according to claim 1, in the step of classifying the charged particles, further comprising the step of modulating an electrostatic field intensity applied to a the conductive cylinder at low frequency and amplifying the electric signal of detecting the charged particles tuned to the low frequency in a narrow band.

* * * * *